US011340205B2

(12) United States Patent
Wu et al.

(10) Patent No.: US 11,340,205 B2
(45) Date of Patent: May 24, 2022

(54) SYSTEMS AND METHODS FOR DETERMINING CONCENTRATIONS OF MATERIALS IN SOLUTIONS

(71) Applicant: Hong Kong Applied Science and Technology Research Institute Co., Ltd., Shatin (HK)

(72) Inventors: Mengting Wu, Yuen Long (HK); Chun Chung Chan, Tseuen Wan (HK); Chun Zhang, Hong Kong (CN)

(73) Assignee: Hong Kong Applied Science and Technology Research Institute Co., Ltd., Shatin (HK)

( * ) Notice: Subject to any disclaimer, the term of this patent is extended or adjusted under 35 U.S.C. 154(b) by 792 days.

(21) Appl. No.: 16/256,455

(22) Filed: Jan. 24, 2019

(65) Prior Publication Data

US 2020/0240970 A1    Jul. 30, 2020

(51) Int. Cl.
*G01N 33/18* (2006.01)
*G01N 21/359* (2014.01)
(Continued)

(52) U.S. Cl.
CPC ......... *G01N 33/1813* (2013.01); *G01N 21/31* (2013.01); *G01N 21/359* (2013.01);
(Continued)

(58) Field of Classification Search
CPC .. G01N 33/1813; G01N 21/31; G01N 21/359; G01N 27/02; G01N 27/023;
(Continued)

(56) References Cited

U.S. PATENT DOCUMENTS 7,351,349 B2    4/2008    Shekel et al.
8,106,361 B2    1/2012    Benes
(Continued)

FOREIGN PATENT DOCUMENTS

CN    1380973 A    11/2002
CN    1518610 A    8/2004
(Continued)

OTHER PUBLICATIONS

China National Intellectual Property Administration, First Office Action issued for Chinese Patent Application No. 201980000295.3, dated Mar. 30, 2021, 10 pages.
(Continued)

*Primary Examiner* — Benjamin R Schmitt
(74) *Attorney, Agent, or Firm* — Norton Rose Fulbright US LLP (57) ABSTRACT

Systems and methods which use an optical sensor and an electromagnetic sensor in cooperation for detecting concentrations of one or more materials in solutions are described. In operation according to embodiments of a cooperative optical and electromagnetic sensor material concentration detector, both an optical sensor and electromagnetic sensor are used in cooperation to detect a concentration of a material having a physical feature that is otherwise incompatible with one or the other sensors and/or a material for which measurement is affected by another material present in the sample. Embodiments are, for example, configured to provide a cooperative implementation of optical and electromagnetic sensors operable to detect concentrations of metal ions and acid in a solution, such as for use in real-time material concentration detection.

27 Claims, 7 Drawing Sheets

(51) Int. Cl.
*G01N 27/02* (2006.01)
*G01N 21/31* (2006.01)

(52) U.S. Cl.
CPC ......... *G01N 27/025* (2013.01); *G01N 33/182* (2013.01); *G01N 2201/062* (2013.01); *G01N 2201/067* (2013.01); *G01N 2201/0694* (2013.01); *G01N 2201/126* (2013.01)

(58) Field of Classification Search
CPC ............... G01N 27/025; G01N 33/182; G01N 2201/062; G01N 2201/067
See application file for complete search history.

(56) References Cited

U.S. PATENT DOCUMENTS

| | | |
|---|---|---|
| 9,297,749 B2 | 3/2016 | Micheels et al. |
| 2002/0084416 A1 | 7/2002 | Kiuchi |
| 2016/0161402 A1 | 6/2016 | Micheels et al. |
| 2017/0102370 A1 | 4/2017 | Alber et al. |
| 2018/0059015 A1 | 3/2018 | Li et al. |

FOREIGN PATENT DOCUMENTS

| | | |
|---|---|---|
| CN | 101170063 A | 4/2008 |
| CN | 101563654 A | 10/2009 |
| CN | 102169102 A | 8/2011 |
| CN | 102445476 A | 5/2012 |
| CN | 101567309 | 10/2012 |
| CN | 102830156 A | 12/2012 |
| CN | 103205769 A | 7/2013 |
| CN | 103335976 A | 10/2013 |
| CN | 103911651 A | 7/2014 |
| CN | 106133202 A | 11/2016 |
| CN | 106796207 A | 5/2017 |
| CN | 107085117 A | 8/2017 |
| CN | 107101956 A | 8/2017 |
| CN | 107130287 A | 9/2017 |
| CN | 107132263 A | 9/2017 |
| CN | 107272755 A | 10/2017 |
| CN | 109923415 A | 6/2019 |
| EP | 0885986 A2 | 12/1998 |
| JP | 2002235194 A | 8/2002 |
| JP | 2003004706 A | 1/2003 |
| JP | 2012037303 A | 2/2012 |
| JP | 2013019009 A | 1/2013 |
| JP | 2013030800 A | 2/2013 |
| KR | 100696000 B1 | 3/2007 |
| KR | 101582098 B1 | 1/2016 |
| KR | 20180057955 A | 5/2018 |
| WO | WO-2008001640 A1 | 1/2008 |

OTHER PUBLICATIONS

Bensalah, W. et al. "Young's Modulus of Anodic Oxide Layers Formed on Aluminum in Sulphuric Acid Bath," Materials Letters, vol. 179, 2016, pp. 82-85, 4 pages.

Luo, et al. "Determination on Content of Free Alkali and Aluminium in Alkaline Etching Solution of Aluminium Anodizing," Electroplating and Finishing, vol. 22, No. 4, 2003, 4 pages.

Vila, J. et al. "Electrical Conductivity of Aqueous Solutions of Aluminum Salts," Physical Review E 71, 031201, 2005, 8 pages.

Gustafson, H. et al. "Determination of Total Dissolved Solids in Water by Electrical Conductivity," Industrial & Engineering Chemistry Analytical Edition, vol. 11, No. 7, 1939, 3 pages.

Frink, C. R. et al. "Hydrolysis of the Aluminum Ion in Dilute Aqueous Solutions," Inorganic Chemistry, vol. 2, No. 3, 1963, 6 pages.

Shinde, S. et al. "A Spectral Probe for Detection of Aluminum (III) Ions Using Surface Functionalized Gold Nanoparticles," Nanomaterials, vol. 7, No. 10, 2017, 16 pages.

International Search Report and Written Opinion issued for PCT Application No. PCT/CN2019/073582, dated Oct. 24, 2019, 11 pages.

| | | | | | | | |
|---|---|---|---|---|---|---|---|
| 40.2 | 0.0 | 180.0 | 5.0 | 40.1 | 0.0 | 179.4 | 5.7 |
| 40.2 | 0.0 | 180.0 | 5.0 | 40.1 | 0.0 | 179.6 | 5.8 |
| 40.2 | 0.0 | 180.0 | 5.0 | 40.1 | 0.0 | 179.6 | 5.8 |
| 46.9 | 0.0 | 210.0 | 5.0 | 47.3 | 0.0 | 211.7 | 5.6 |
| 46.9 | 0.0 | 210.0 | 5.0 | 47.3 | 0.0 | 211.9 | 5.5 |
| 46.9 | 0.0 | 210.0 | 5.0 | 47.2 | 0.0 | 211.5 | 5.6 |
| 46.9 | 0.0 | 210.0 | 5.0 | 47.2 | 0.0 | 211.5 | 5.6 |
| 40.2 | 0.0 | 180.0 | 15.0 | 40.5 | 0.0 | 181.5 | 15.4 |
| 40.2 | 0.0 | 180.0 | 15.0 | 40.5 | 0.0 | 181.6 | 15.2 |
| 40.2 | 0.0 | 180.0 | 15.0 | 40.5 | 0.0 | 181.4 | 15.2 |
| 40.2 | 0.0 | 180.0 | 15.0 | 40.5 | 0.0 | 181.4 | 15.1 |
| 46.9 | 0.0 | 210.0 | 15.0 | 46.6 | 0.0 | 208.7 | 15.2 |
| 46.9 | 0.0 | 210.0 | 15.0 | 46.6 | 0.0 | 208.7 | 15.0 |
| 46.9 | 0.0 | 210.0 | 15.0 | 46.5 | 0.0 | 208.3 | 15.0 |
| 46.9 | 0.0 | 210.0 | 15.0 | 46.5 | 0.0 | 208.2 | 14.9 |
| | | | SD = | 0.3 | 0.0 | 1.4 | 0.5 |

Parameters (Abs -> Con):

| kt01 | kt02 | kt03 | c1 | c2 | c3 | c4 |
|---|---|---|---|---|---|---|
| 0.0000 | 0.0000 | 0.0000 | 0.00 | 0.00 | 0.00 | 0.00 |
| 0.0000 | 0.0000 | 0.0000 | 0.00 | 45.18 | 85.11 | 118.14 |
| 0.0000 | 0.0000 | 0.0000 | 0.00 | -11.91 | 93.90 | -57.49 |
| 0.0000 | 0.0000 | 0.0000 | 0.00 | 10.09 | 19.00 | 26.38 |

... prediction completed

SYSTEMS AND METHODS FOR DETERMINING CONCENTRATIONS OF MATERIALS IN SOLUTIONS

TECHNICAL FIELD

The present invention relates generally to detecting concentrations of one or more materials in solutions and, more specifically, to deriving concentrations of materials in solutions using an optical sensor and an electromagnetic sensor in cooperation.

BACKGROUND OF THE INVENTION

It is often desirable, and many times even critical, to know the concentrations of one or more materials in solutions. For example, detecting concentrations of various materials in water may be important to maintaining water quality, such as for water used in various apparatus, in a fresh water supply, etc. Likewise, detecting concentrations of materials in solutions used in an industrial process may be desired, such as to ensure proper operation of the process, process efficiency, quality of the resulting product, etc.

One example of an industrial process in which monitoring of materials in a solution may be desired is the anodizing process. Anodizing is an electrolytic passivation process used to form a hard oxide film on the surface of a metal (e.g., aluminum) which provides anticorrosion protection, and which may be painted or dyed in any color. In operation of an aluminum anodizing process, for example, an anodized aluminum layer is grown by passing a direct current through an electrolytic solution, with the aluminum object serving as the anode. The electrolyte solution used in such an anodizing process typically contains various materials, including an acid (e.g., sulfuric acid, $H_2SO_4$) and metal ions (e.g., aluminum ions, $Al^{3+}$).

Conditions such as acidity, solution temperature, material concentration in the electrolyte, and current may be controlled to facilitate the formation of a consistent oxide layer by the anodizing process. The concentrations of the materials in the electrolyte, however, continuously change during the anodizing process. For example, the concentration of sulfuric acid will decrease and aluminum ions will increase during the anodization process, which will directly affect the thickness of the aluminum oxide and the oxide film quality. Accordingly, monitoring the concentration of materials, such as sulfuric acid and aluminum ions, in real time may be useful in maintaining the yield and quality of the product.

Titration is the traditional method using in determining material concentration with respect to anodizing processes. In particular, the common titration methods are manual titration and automatic potentiometric titration. Both of these titration methods consume additional chemicals for dilution, pH balancing, chemical reaction, and color indication, etc., resulting costs for chemical consumables and chemical waste treatments. Also, titration often introduces subjective error with respect to the measurement of material concentration in a solution. Manual titration methods may have subjective error with respect to the measurement of material concentration in a solution, such as due to personal judgements from person to person. For example, in the analysis of the key points in the process, some people have deeper discrimination on the color of the indicator, and some people are shallower; some people prefer to subconsciously control the subsequent titration process based on the previous titration result, resulting higher or lower in systematic measurement results. The typical sampling frequency in manual titration methods is low (e.g., two times per day), and the sampling process requires appreciable time to complete (e.g., 10 min for the titration test to be performed in the laboratory). Accordingly, manual titration cannot be applied for on-line monitoring for obtaining concentration information timely, such as for timely monitoring and adjusting the concentrations of electrolytes in an industrial process. Compared with manual titration, automatic potentiometric titration is much more accurate and precise. However, although automatic potentiometric titration can detect the target substance in the ppm level, automatic potentiometric titration has relatively high requirements on the instrument such that the cost and maintenance requirements (e.g., requiring frequent daily maintenance) can be very high. Thus, titration methods may not suitable for monitoring solution concentration in real-time in various processes.

An analyzer using an optical sensor, such as an ultraviolet-visible spectroscopy (UV-VIS) analyzer or a visible near infra-red (VIS-NIR) analyzer, may be used for measuring the concentration of certain chemicals by calculating the amount of light absorption. Such analyzers, however, comprise a spectrometer having complex processing and optical sensor systems adapted for use with a wide range of materials and thus are often relatively expensive. Optical analyzers are ineffective with respect to measuring concentrations of material having particular physical features (e.g., colorless, as may defined as having no obvious absorption peak in the UV-VIS-NIR range (200-1700 nm), such as aluminum ions). Operation of some optical analyzers require additional chemicals to be added to the observed solution and/or require chemical reactions. Optical analyzers, therefore, are not suitable for monitoring concentrations of materials in some solutions, such as the above mentioned electrolyte solutions.

A number techniques that detect concentration of a material in a solution have been discussed in various literature, such as patent publications JP2002235194A, US20160161402A1, CN106133202, KR1020180057955, EP0885986, and US7351349 (the disclosures of which are hereby incorporated herein by reference). Such techniques, however, do not provide for determining concentrations of acid (e.g., sulfuric acid) and metal ions (e.g., aluminum ions) in a solution using optical absorption and electromagnetic induction for on-line monitoring of material concentrations in a solution (e.g., real-time monitoring of sulfuric acid and aluminum ion concentrations in an anodizing solution). JP2002235194A, for example, uses electrical conductivity, specific gravity, sound velocity and viscosity for determining material concentrations, and thus relies upon physical properties of the media which requires independent test tanks for measuring and is a relatively complex and expensive system. US20160161402A1 uses near-infrared transmission spectroscopy with respect to samples placed in a sample holder to identify solid or liquid material, and thus provides for optical absorption only and cannot probe aluminum ion concentrations. CN106133202 uses voltage-current tests to control the concentration of sulfuric acid in an anodizing system, wherein the voltage-current tests cannot probe for both aluminum ion and sulfuric acid concentrations. KR1020180057955 uses optical, electrical, and ultrasonic detection techniques, wherein the contact-type electrodes of the electrical detection system are not suitable for use with respect to high concentrations of acid, and the optical sensor uses only a pair of prisms to obtain optical data which is ineffective for use with respect to separating complex composition solutions. EP0885986 uses a light emission and receiving device to measure hypochlorous acid concentration, and thus provides for optical absorption only and cannot probe aluminum ion concentrations. US7351349 uses near-infrared radiation to detect a change in an optical property of a chemical component, and thus provides for optical absorption only and cannot probe aluminum ion concentrations.

BRIEF SUMMARY OF THE INVENTION

The present invention is directed to systems and methods which use an optical sensor and an electromagnetic sensor in cooperation for detecting concentrations of one or more materials in solutions. Cooperative optical and electromagnetic sensor material concentration detectors (also referred to herein as "cooperative op-el mat-con detectors") of embodiments of the invention are configured for detecting concentrations of a material having a particular physical feature, such as being colorless, for which one or the other of the sensors thereof is ineffective in directly or solely detecting concentration of the material. Cooperative op-el mat-con detectors of embodiments are additionally or alternatively configured for detecting concentrations of a material for which measurement of by one or the other of the sensors can be affected by another material in a solution sampled.

In operation according to embodiments of the invention, both the optical sensor and electromagnetic sensor are used in cooperation to detect a concentration of the material having a physical feature that is otherwise incompatible with one or the other sensors and/or a material for which measurement is affected by another material present in the sample. For example, an optical sensor may be ineffective in directly or solely detecting a concentration of a colorless material (e.g., metal ions, such as aluminum ions) in a solution. Further, an electromagnetic sensor may be ineffective in accurately detecting a concentration of one or more of two materials (e.g., metal ions, such as aluminum ions, or acid, such as sulfuric acid) when both are present, particularly when concentrations are varying. Nevertheless, a concentration of a material, such as the aforementioned colorless metal ions, may be detected by a cooperative op-el mat-con detector of embodiments of the invention through operation to combine (e.g., subtract) measurement data provided by each of the optical and electromagnetic sensors. Accordingly, a cooperative op-el mat-con detector may derive the concentration of a particular material using a combination of optical data and electromagnetic data.

Embodiments of the invention are, for example, configured to provide a cooperative implementation of optical and electromagnetic sensors operable to detect concentrations of metal ions and acid in a solution. As a specific example, the solution may comprise an anodizing solution used in an aluminum anodizing process, wherein concentrations of aluminum ions ($Al^{3+}$) and sulfuric acid ($H_2SO_4$) are detected.

Cooperative op-el mat-con detectors of embodiments are configured to facilitate real-time material concentration detection, such as to accommodate analysis of a solution as it is used in an industrial or other process. As a specific example, concentrations of aluminum ions and sulfuric acid may be detected by an embodiment of a cooperative op-el mat-con detector in real-time operation of an anodizing process.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present disclosure, reference is now made to the following descriptions taken in conjunction with the accompanying drawings, in which.

DETAILED DESCRIPTION OF THE INVENTION

Figure 1:
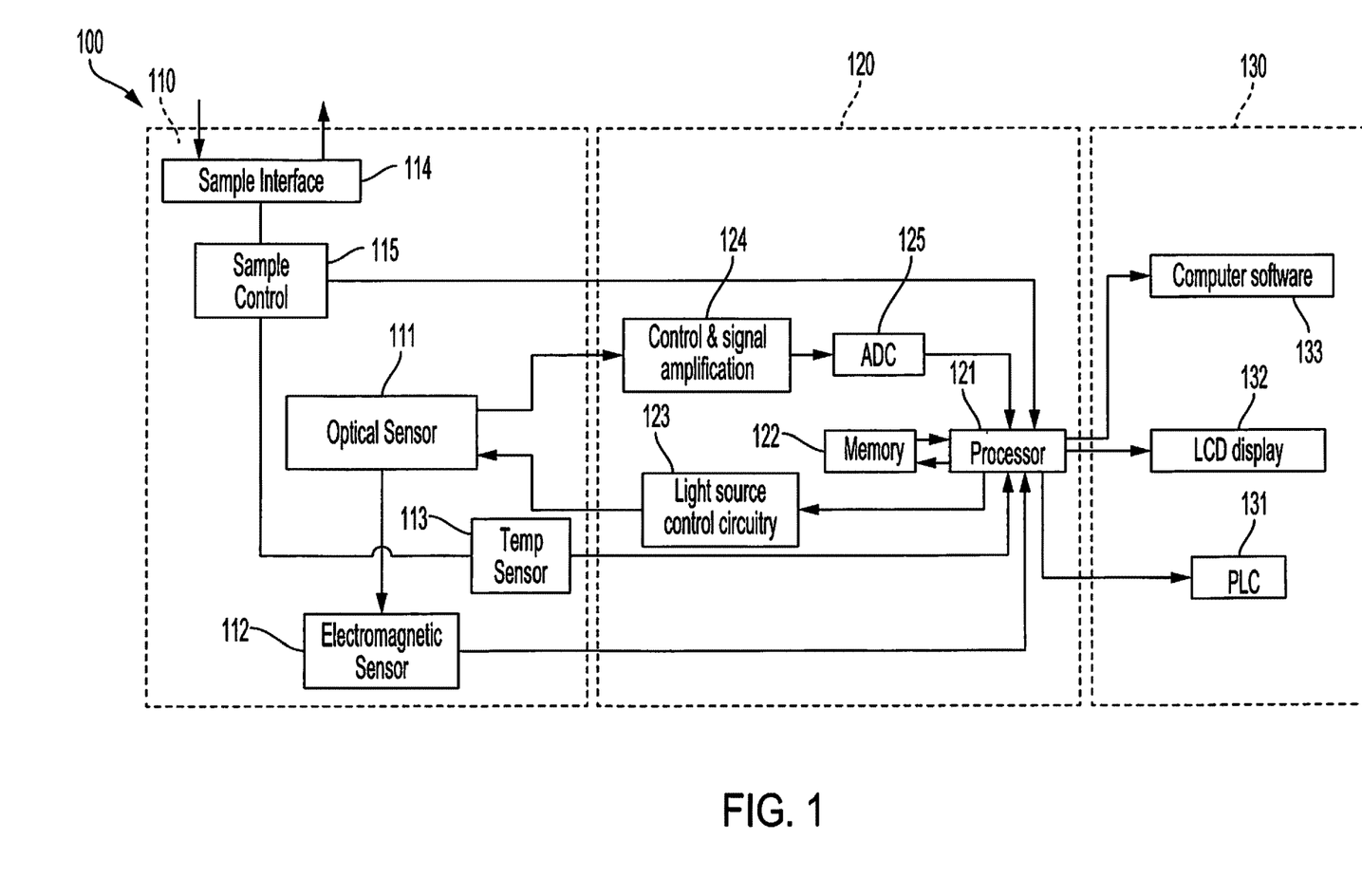
FIG. 1 shows a cooperative optical and electromagnetic sensor material concentration detector configuration of embodiments of the present invention.

An embodiment of a cooperative optical and electromagnetic sensor material concentration detectors (also referred to as "cooperative op-el mat-con detectors") configured to use an optical sensor and an electromagnetic sensor in cooperation for detecting concentrations of one or more materials in solutions according to concepts of the present invention is shown in FIG. 1. In particular, cooperative op-el mat-con detector 100 of the illustrated embodiment is shown comprising sensor unit 110, control unit 120, and user interface unit 130.

Sensor unit 110 of cooperative op-el mat-con detector 100 includes a plurality of sensors for measurement of various aspects of materials in a sample, wherein data provided by two or more of the sensors is used cooperatively for detecting concentrations of a material having a particular physical feature for which one or another of the sensors is ineffective in directly or solely detecting concentration of the material and/or a material for which measurement by one or another of the sensors is affected by another material present in the sample. Sensor unit 110 of the illustrated embodiment includes optical sensor 111, electromagnetic sensor 112, and temperature sensor 113, each of which may be operated to measurement one or more aspects of materials in a solution being sampled. Optical sensor 111 and electromagnetic sensor 112 may, for example, be utilized cooperatively for detecting concentrations of a material having a physical feature (e.g., colorless material) for which optical sensor 111 is ineffective in detecting and/or which is in the presence of another material (e.g., acid) affecting measurement of the material by electromagnetic sensor 112. Temperature sensor 113 may be utilized to provide data useful in configuring and/or controlling operation of aspects of cooperative op-el mat-con detector 100, such as to provide temperature data for compensating for the effects of temperature on operation of the detector and/or components thereof (e.g., optical sensor 111 and/or electromagnetic sensor 112).

It should be appreciated that the various sensors (e.g., optical sensor 111, electromagnetic sensor 112, and temperature sensor 113) of sensor unit 110 of embodiments may be arranged in various configurations. For example, optical sensor 111 and electromagnetic sensor 112 may be provided in a parallel configuration, as shown in the example embodiment of FIG. 2A, or in a series configuration, as shown in the example embodiment of FIG. 2B. In the parallel configuration of FIG. 2A, the sample flow path within the sensor unit from/to sample interface 114 is split so that the sample material (e.g., liquid of a sampled solution) is split to provide sample material to each of optical sensor 111 and electromagnetic sensor 112 in parallel. Such a parallel configuration with respect to these sensors may be utilized to solve flow-rate-difference issues between electrical and optical measurements. Moreover, the parallel configuration accommodates changing sensor modules (e.g., optical sensor 111 and/or electromagnetic sensor 112) to provide sensor modules having flow rates and other characteristics (e.g., operating frequency range, sensitivity, etc.) configured for the particular solutions and materials to be sampled. In the series configuration of FIG. 2B, the sample flow path within the sensor unit from/to sample interface 114 is consecutive to provide sample material to each of optical sensor 111 and electromagnetic sensor 112 in sequence. Such a series configuration with respect to these sensors provides a simpler configuration to implement (e.g., may omit a manifold facilitating separate sample flows and flow rates), but requires the sample cavity, flow rates, detection interval, and/or hardware for both sensors to be designed for a specific solution or production line and must be redesigned if other production lines or solutions having different materials and concentrations are to be sampled.

Figure 2A:
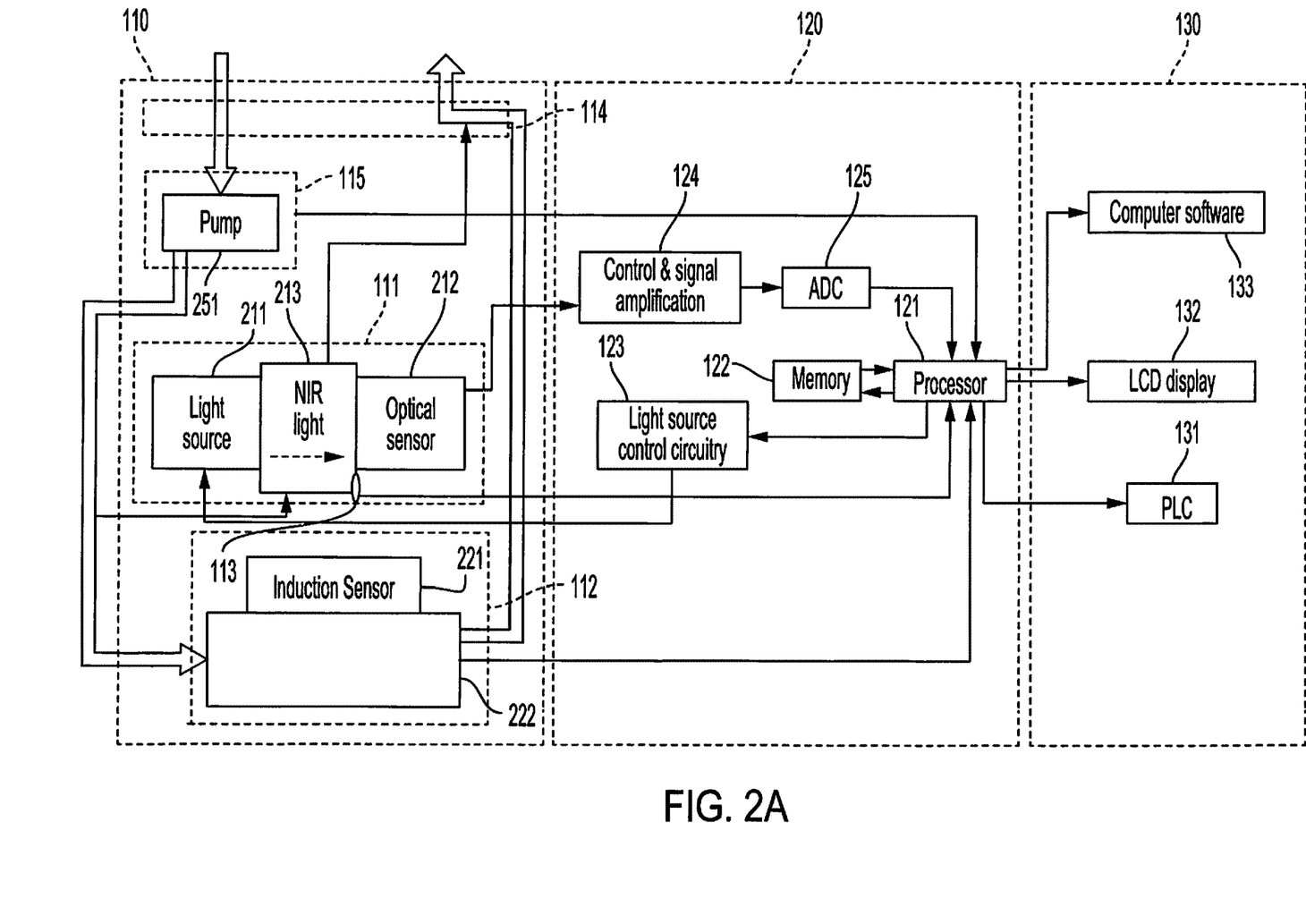
FIGS. 2A and 2B show detail with respect to optical sensor unit configurations of cooperative optical and electromagnetic sensor material concentration detectors of embodiments of the present invention.
Figure 2B:
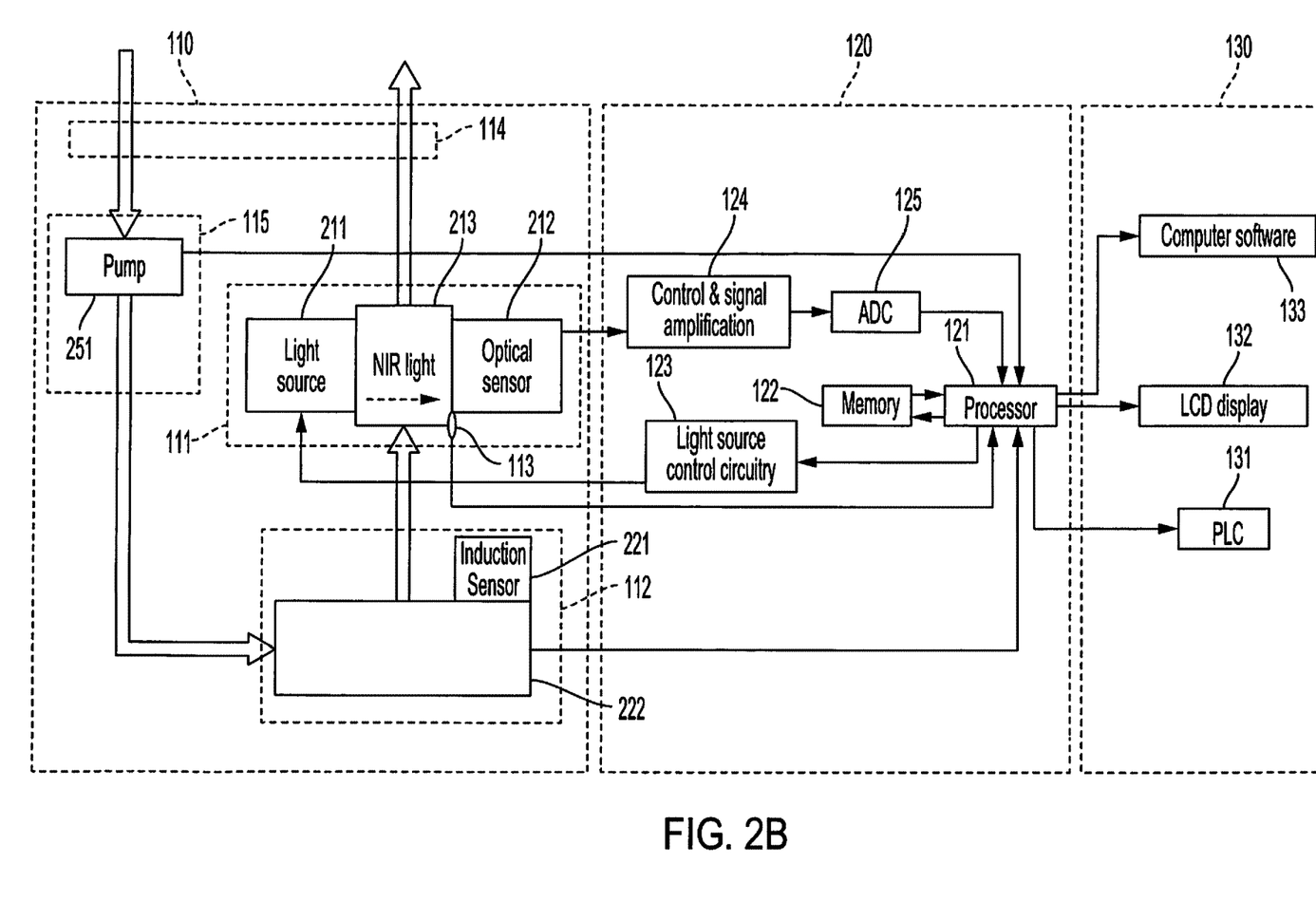

Optical sensor 111 of embodiments comprises a sensor assembly configured for measurement by optical absorption. Accordingly, optical sensor 111 may comprise a light source and optical receiver juxtaposed with respect to a sample cavity (e.g., disposed behind two parallel windows on opposing sides of the sample cavity) for passing light radiated by the light source through a sample disposed in the sample cavity for reception by the optical receiver. An example of such a configuration of optical sensor 111 is shown in the embodiment of FIGS. 2A and 2B, wherein optical sensor 111 includes light source 211, optical receiver 212, and sample cavity 213. Light source 211 and optical receiver 212 of optical sensor 111 of embodiments may operate in the ultraviolet (UV), visible (VIS), and/or near infra-red (NIR) spectrums. For example, light source 211 may comprise one or more light emitting diode (LED) and optical receiver 212 may comprise one or more photodiode (e.g., embodiments may use two instances of a LED, wherein one instance is configured and disposed to operate as a UV, VIS, and/or NIR light emitter and one instance is configured and disposed to operate as a UV, VIS, and/or NIR optical receiver). The particular LED/photodiode combination utilized with respect to any particular implementation of optical receiver 212 may be selected for use with a particular solution or material to be sampled, and thus may be relatively narrow band or otherwise provide an economical implementation. For example, the LED/photodiode of an implementation adapted for use with respect to anodizing solution comprising sulfuric acid and aluminum ions may be configured for operation at 1450 nm or 1600 nm.

The light source, optical receiver, and sample cavity configuration of embodiments provides a flow cell implementation of optical sensor 111, wherein a solution being sampled may be continuously or controllably passed through optical sensor 111 (e.g., via sample cavity 213) for measurement (e.g., for real-time sampling of material concentration). The optical path of an embodiments of such a flow cell implementation is preferably short if the material concentration is relatively high (e.g., the width of sample cavity 213 where light source 211 and optical sensor 212 are disposed in juxtaposition may be in the range of 0.01 mm to 50 mm, such as 2 mm providing flow cell having an approximately 0.8 ml sample cavity in some embodiments) and precise (e.g., precisely aligned light source and optical receiver disposed behind parallel windows of optical glass, quartz, or other suitable material) to facilitate high sensitivity using a relatively small flow of sample material.

Electromagnetic sensor 112 of embodiments comprises a sensor assembly configured for measurement by induction. An example of such a configuration of electromagnetic sensor 112 is shown in the embodiment of FIGS. 2A and 2B, wherein electromagnetic sensor 112 is shown as comprising induction sensor 221 and sample cavity 222. Induction sensor 221 of embodiments may, for example, comprise an oscillator formed from a magnetic substance that is configured to move relative to one or more coils when in proximity to particular materials (e.g., different metals). A specific example of a sensor that uses electromagnetic induction and can measure high concentration values is the MDM-25A electromagnetic conductivity meter made available from DKK-TOA CORPORATION, Japan, capable of 0 to 2000 mS/cm measurements at temperatures of −5 degrees Celsius to 120 degrees Celsius.

Induction sensor 221 (e.g., using a oscillator and coil configuration) of embodiments provides a non-contact implementation of electromagnetic sensor 112, wherein a solution being sampled may be continuously or controllably passed through electromagnetic sensor 112 (e.g., via sample cavity 222) for measurement (e.g., for real-time sampling of material concentration without requiring contact between the sensor and the sampled material) without the material contacting induction sensor 221 (e.g., contact between the induction sensor and corrosive or other harmful materials in the sample is avoided). Embodiments of inductive sensor 221 may utilize a relatively large sample volume (e.g., a flow cell having an approximately 200 ml sample cavity) for performing induction based measurement (e.g., measurement of electromagnetic conductivity and/or flow rate). Accordingly, sample cavity 222 of embodiments of electromagnetic sensor 112 is appropriately sized for containing a corresponding volume of sample material.

Temperature sensor 113 of embodiments comprises a sensor assembly configured for measurement of temperature (e.g., temperature of sample material, operating temperature of another sensor of the sensor unit, and/or the like). Accordingly, temperature sensor 113 may comprise a thermally sensitive resistor (thermistor), a resistance temperature detector (RTD) element, a thermocouple, semiconductor-based temperature sensor, infrared sensitive thermopile, etc. Temperature sensor 113, comprising one or more of the above sensor elements, may be disposed to contact a solution being sampled, to contact the container incarcerating the solution, to perform temperature measurement through non-contact, etc. For example, the example embodiments shown in FIGS. 2A and 2B provide configurations in which temperature sensor 113 is disposed to measure temperature within sample cavity 213 of optical sensor 111 to thereby provide temperature information relevant to the operation of optical sensor 111.

Although the exemplary embodiments illustrated in FIGS. 1, 2A, and 2B show one instance each of optical sensor 111, electromagnetic sensor 112, and temperature sensor 113, it should be appreciated that embodiments may comprise more or fewer instances of these or other sensors, as appropriate to the material sampled, the sampling conditions, etc. As but one example, a second instance of temperature sensor 113 may be utilized. Embodiments of cooperative op-el mat-con detector 100 have an instance of temperature sensor 113 disposed within a housing of electromagnetic sensor 112 (e.g., electromagnetic sensor 112 may be provided as a commercially available sensor package including an inductive sensor and temperature sensor) to provide temperature information relevant to the operation of electromagnetic sensor 112.

In addition to the actual sensors used for measuring various aspects of materials in a sample, sensor unit 110 of embodiments may comprise additional components useful for facilitating measurements in accordance with the concepts herein. For example, sensor unit 110 of the illustrated embodiment includes sample interface 114 and sample control system 115. Sample interface 114 may, for example, comprise a sample input lumen and sample output lumen, such as for coupling with a solution pathway or reservoir used by a process in which material concentration is to be measured by cooperative op-el mat-con detector 100. Correspondingly, sample control system 115 may comprise apparatus, such as one or more valves, pumps, manifolds, etc., utilized in directing sample media to the sensors of cooperative op-el mat-con detector 100. Some or all of the remaining componentry of sensor unit 110 is preferably coupled to (e.g., in fluid communication with) sample interface 114 and/or sample control system 115.

Control unit 120 of cooperative op-el mat-con detector 100 includes one or more processors and associated componentry for detecting concentrations of materials using the sensors of sensor unit 110. Control unit 120 of the illustrated embodiment, for example, includes processor 121 and associated memory 122 to provide various control aspects with respect to detecting concentrations of materials by cooperative op-el mat-con detector 100. Componentry, such as light source control circuitry 123, control and signal amplification circuitry 124, and analog to digital converter (ADC) 125 of the illustrated embodiment, is included to facilitate operation of processor 121 in implementing material concentration detection using the sensors of sensor unit 110. Although not shown in the exemplary embodiment of FIG. 1, similar additional componentry may be utilized with respect to other of the sensors, as appropriate. For example, one or more ADCs may be utilized with respect to electromagnetic induction sensor 112 and/or temperature sensor 113 where these sensors provide analog measurement signals. Such additional componentry may be disposed within sensor unit 110, such as within one or more of a corresponding optical sensor housing, electromagnetic sensor housing, and/or temperature sensor housing, according to embodiments.

Processor 121 may be operated to control aspects of sampling materials, collecting sampled data, processing collected data, and outputting processed data in accordance with concepts described herein. Embodiments of processor 121 may comprise one or more general purpose processor (e.g., CORE processor available from Intel Corporation, RADEON processor available from Advanced Micro Devices, Inc., POWERPC processor available from International Business Machines, advanced reduced instruction set computer machine (ARM) central processing unit (CPU) core, and/or the like) and/or one or more special purpose processor (e.g., application specific integrated circuit (ASIC), field programmable gate array (FPGA), graphics processing unit (GPU), and/or the like). Memory 122 may comprise any processor readable memory (e.g., random access memory (RAM), read only memory (ROM), flash memory, magnetic memory, optical memory, and/or the like) suitable for use with respect to processor 121 for storing one or more instruction sets (e.g., application software, firmware, operating system, applets, and/or the like), data (e.g., configuration parameters, operating parameters, collected data, processed data, and/or the like), etc.

Processor 121 of embodiments may interface directly with various other componentry of cooperative op-el mat-con detector 100. For example, processor 121 of the embodiment illustrated in FIG. 1 is interfaced directly with electromagnetic sensor 112 for controlling measurements with respect to sampled media and obtaining data therefrom. Additionally, processor 121 of the illustrated embodiment is interfaced directly with sample control system 115 to control the introduction and/or flow of sample media with respect to sensor unit 110.

Additionally or alternatively, processor 121 of embodiments may utilize additional componentry for interfacing with various other componentry of cooperative op-el mat-con detector 100. For example, processor 121 of the embodiment illustrated in FIG. 1 is interfaced with optical sensor 111 via light source control circuitry 123, control and signal amplification circuitry 124, and ADC 125. Light source control circuitry 123 may, for example, comprise circuits for driving and current control, timing control of light source(s), etc. operating under control of processor 121 to control light emission by a light source of optical sensor 111. Control and signal amplification circuitry 124 of embodiments may comprise filters, amplifiers, ambient light cancellation circuits, etc. operating under control of processor 121 to control reception of light by an optical receiver of optical sensor 111, provide processing of signals therefrom, etc. Likewise, ADC 125 may comprise an analog to digital conversion circuit operating under control of processor 121 to provide conversion of analog signals to digital data, such as may be suitable for storage, processing, and analysis by processor 121.

Processor 121 of embodiments may additionally interface with componentry of a user interface. For example, processor 121 of the embodiment illustrated in FIG. 1 is interfaced with programmable logic controller (PLC) 131, display 132, and user interface software 133 of user interface 130. PLC 131 of embodiments may comprise a processor-based system (e.g., industrial digital computer) utilized in controlling one or more aspects of a process. Additionally or alternatively, PLC 131 of embodiments may comprise a general purpose processor-based terminal, such as a personal computer (PC), notebook computer, tablet device, smart phone, personal digital assistant (PDA), etc., utilized in various applications. The illustrated embodiment of PLC 131 and/or processor 121 may operate under control of user interface software 133 for coordinating interfacing between cooperative op-el mat-con detector 100 and a user thereof. Display 132 may be utilized with respect to PLC 131 and/or processor 121 in displaying data and other relevant information users of cooperative op-el mat-con detector 100.

It should be appreciated that, although the embodiment illustrated in FIG. 1 includes user interface 130, such a user interface or some portion thereof may be omitted in some implementations. For example, display 132 and user interface software 133 may be utilized in an embodiment without PLC 131, such as where output of data and other relevant information to users is desired without accommodating user control of cooperative op-el mat-con detector 100. Where an embodiment of cooperative op-el mat-con detector 100 is operated in an autonomous configuration, without user control and user monitoring, user interface 130 may be omitted. Embodiments, however, may accommodate removable connection of user interface 130 or components thereof, such as for providing a user interface as needed.

Cooperative op-el mat-con detector 100 of the embodiment of FIG. 1 is configured to use optical sensor 111 and electromagnetic sensor 112 in cooperation for detecting concentrations of one or more materials in solutions. For example, optical sensor 111 and electromagnetic sensor 112 of sensor unit 110 may be utilized to measure concentrations of a material having a particular physical feature, such as being colorless, for which optical sensor 111 is ineffective in directly or solely detecting concentration of the material. Additionally or alternatively, optical sensor 111 and electromagnetic sensor 112 of sensor unit 110 may be utilized to measure concentrations of a material for which measurement by electromagnet sensor 112 is affected by another material present in the sample. In operation according to embodiments of cooperative op-el mat-con detector 110, both optical sensor 111 and electromagnetic sensor 112 are used in cooperation to detect a concentration of such a material (e.g., metal ions, such as aluminum ions, as may be in a solution also including acid, such as sulfuric acid) that is otherwise incompatible with measurement by either optical sensor 111 or electromagnetic sensor 112 alone. For example, a concentration of such a material may be detected by a cooperative op-el mat-con detector 110 of embodiments through operation (e.g., by processor 121 of control unit 120) to combine (e.g., subtract) measurement data provided by each of optical sensor 111 and electromagnetic sensor 112. Accordingly, a cooperative op-el mat-con detector may derive the concentration of a particular material using a combination of optical data and electromagnetic data, such as may be stored in memory 122 and/or output or otherwise utilized by user interface unit 130.

Having described configurations of cooperative op-el mat-con detectors of embodiments of the present invention above, operation of such cooperative op-el mat-con detectors will be described below. In order to aid in understanding operation of embodiments of cooperative op-el mat-con detectors, operation with respect to an example solution in which a sample material for which concentration data is to be determined has a particular physical feature for which one or the other of the sensors of cooperative op-el mat-con detector 100 is ineffective in directly or solely detecting concentration of the material and/or a material for which measurement is affected by another material present in the sample. For example, in the exemplary operation described below it is assumed that optical sensor 111 is ineffective in directly or solely detecting a concentration of a colorless material (e.g., metal ions, such as aluminum ions) in a solution. Nevertheless, the exemplary operation of cooperative op-el mat-con detector 100 detects the concentration of such a material through utilizing optical sensor 111 and electromagnetic sensor 112 in cooperation. It should be appreciated that the concepts of the present invention are applicable to materials and/or physical features different than those in the exemplary operation described.

Metal ions (e.g., aluminum ions) are an example of colorless materials for which material concentration measurements may be desired while the material is in the presence of one or more other materials for which measurement is affected with respect to one or more sensors. For example, monitoring of materials in a solution may be desired in an anodizing process, in which an electrolytic passivation process using an electrolyte solution comprising an acid (e.g., sulfuric acid, $H_2SO_4$) and metal ions (e.g., aluminum ions, $Al^{3+}$) to form a hard oxide film on the surface of a metal (e.g., aluminum). During the anodizing process, the concentration of acid (e.g., $H_2SO_4$) will decrease in the electrolyte solution and the concentration of metal ions (e.g., $Al^{3+}$) will increase in the electrolyte solution. Such variations in these materials can directly affect the oxide film quality, giving different thickness, as shown in the table below for an aluminum anodizing process. The optimal concentration of the aforementioned materials in the electrolyte solution of such an aluminum anodizing process are $H_2SO_4$: 160-230 g/L and $Al^{3+}$: 3-20 g/L.

| | High $H_2SO_4$ | Optimum | Low $H_2SO_4$ |
|---|---|---|---|
| Concentration of acid in electrolyte solution | High $H_2SO_4$ concentration (greater than 230 g/L) | Optimum $H_2SO_4$ concentration (160-230 g/L) | Low $H_2SO_4$ concentration (0-160 g/L) |
| Concentration of metal ions in electrolyte solution | Low $Al^{3+}$ concentration (0-3 g/L) | Optimum $Al^{3+}$ concentration (3-20 g/L) | High $Al^{3+}$ concentration (greater than 20 g/L) |
| Consequences | Oxide film absorption capacity is low, affecting dyeing process. | Suitable oxide film thickness, corrosion resistance. | Insufficient film thickness, high power consumption and may cause burns on the film. |

As can be appreciated from the foregoing, it may be desirable to monitor the concentrations of $Al^{3+}$ and $H_2SO_4$ for use in providing control to maintain the materials at the optimal range. However, electromagnetic induction data can be affected by $H_2SO_4$ and $Al^{3+}$ at the same time, especially when concentrations are varying. Accordingly, the concentration of $Al^{3+}$ in such an electrolytic solution cannot be determined only by an electromagnetic induction sensor in light of the presence of $H_2SO_4$. Further, the concentration of $Al^{3+}$ cannot be determined only by an optical sensor in light of the material having no obvious absorption peak in the UV-VIS-NIR range (200-1700 nm) (i.e., the material being colorless).

The sample volume and flow rate are generally different in optical and electromagnetic measurement, suggesting that such measurement techniques are not well suited for use together (e.g., their separate use is typically more appropriate). Nevertheless, cooperative op-el mat-con detector 100 of embodiments shown in FIGS. 1, 2A, and 2B uses optical sensor 111 in cooperation with electromagnetic sensor 112 for determining concentrations of $H_2SO_4$ and $Al^{3+}$ in a solution, online by a combination of optical absorption and electromagnetic induction. Although optical measurement methods are typically not viable for probing the concentration of aluminum ions and electromagnetic measurement methods may give ambiguity in probing a sample liquid with high concentration of acids for which the response is non-linear, embodiments of a cooperative op-el mat-con detector implement a configuration in which these measurement methods are used in cooperation. Cooperative op-el mat-con detector 100 of embodiments is therefore configured to facilitate the cooperative use of both optical measurement and electromagnetic methods. For example, temperature sensor 113 is utilized (e.g., in a temperature compensation method) according to embodiments to resolve issues with respect to temperature effects on the optical measurement and electromagnetic measurements. Further, the measurement with respect to a particular material made by the optical sensor and the electromagnetic sensor are based upon different physical properties of that material, and thus are not readily combined. Embodiments of cooperative op-el mat-con detector 100 therefore implement normalization, preferably in combination with the above mentioned temperature compensation method, in facilitating cooperative use of the optical and electromagnetic sensors. Additionally, embodiments of cooperative op-el mat-con detector 100 may implement different sample material flows to accommodate differences in the measurement characteristics of the optical and electromagnetic methods. As a specific example, embodiments may use the parallel configuration of FIG. 2A to facilitate a short and precise optical path with respect to optical sensor 111 while a large sample volume is nevertheless provided with respect to electromagnetic sensor 112 to facilitate induction based electromagnetic measurement.

Figure 3:
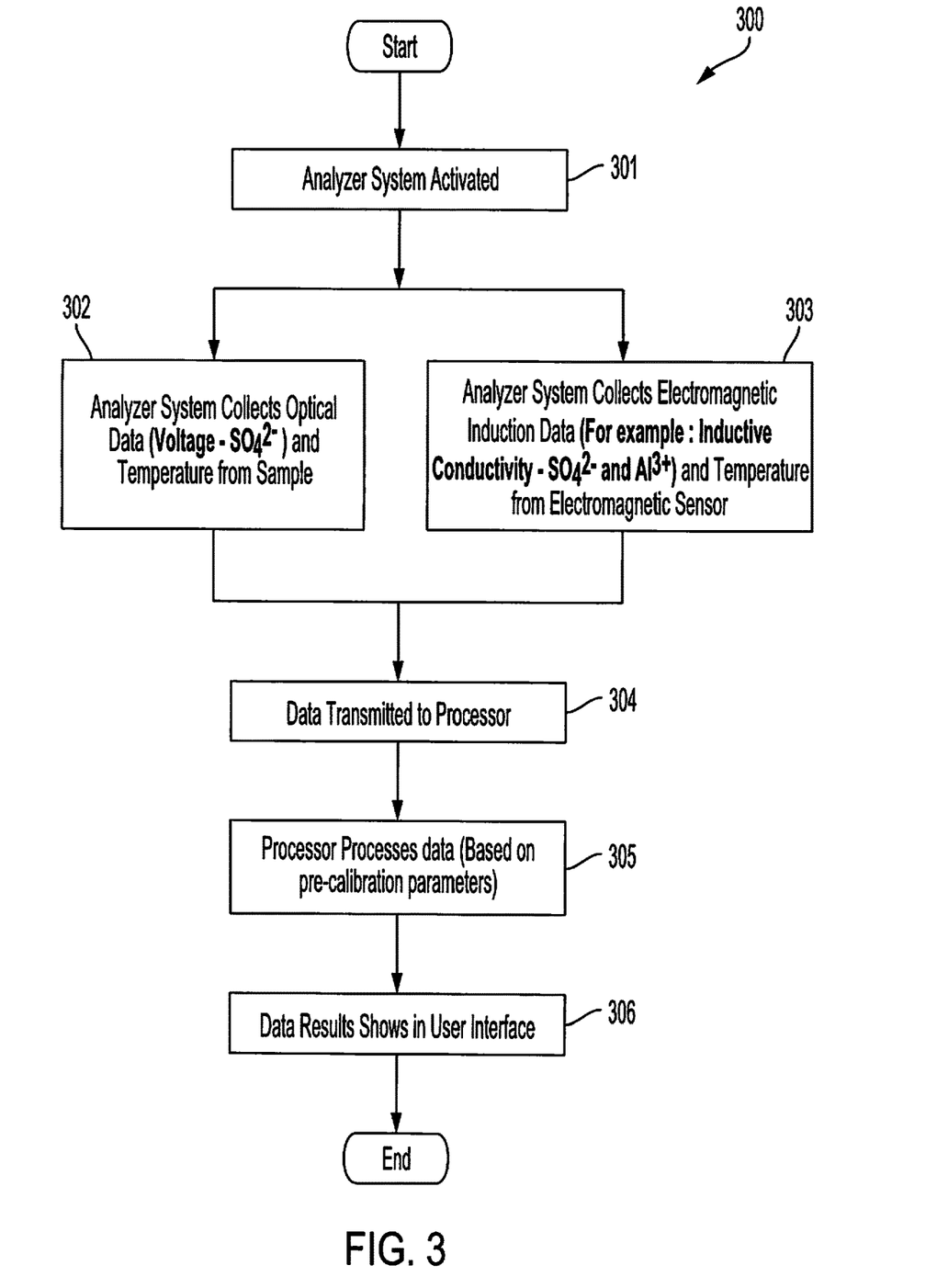
FIG. 3 shows a flow diagram of operation of a cooperative optical and electromagnetic material concentration detector of embodiments of the invention.

FIG. 3 shows flow 300 providing operation of embodiments of cooperative op-el mat-con detector 100. In particular, the exemplary operations of flow 300 use optical sensor 111 in cooperation with electromagnetic sensor 112 for determining concentrations of $H_2SO_4$ and $Al^{3+}$ by a combination of optical absorption and electromagnetic induction.

At block 301 of the illustrated embodiment, cooperative op-el mat-con detector 100 is activated. For example, processor 121 of control unit 120 may operate under control of an instruction set to initialize various components of sensor unit 110, control unit 120, and/or user interface 130 for material concentration measurement. Such initialization may include loading parameters (e.g., calibration parameters, operating parameters, etc.) for use in measurements with respect to a particular material (e.g., the acid of the electrolytic solution) by optical sensor 111 (e.g., using a NIR LED/photodiode implementation) and by electromagnetic sensor 112 (e.g., using an induction sensor implementation). The initialization may additionally or alternatively include controlling changing from idle an state to an active state of various components (e.g., optical sensor 111, electromagnetic sensor 112, light source control circuitry 123, control and signal amplification circuitry 124, ADC 125, etc.) in preparation of operation of cooperative op-el mat-con detector 100. Processor 121 may likewise operate under control of an instruction set to initiate operation of various components of sensor unit 110, control unit 120, and/or user interface 130 for material concentration measurement. Such operation initiation may include controlling sample control system 115 (e.g., by engaging pump 251) to cause sample material to be presented to the sensors of sensor unit 110. The operation initiation may additionally or alternatively include controlling optical sensor 111, electromagnetic sensor 112, and temperature sensor 113 to begin sensing operation (e.g., as may be performed via various control circuitry, such as light source control circuitry 123 and control and signal amplification circuitry 124, such as in the case of optical sensor 111).

Cooperative op-el mat-con detector 100 operates to collect sensor data at blocks 302 and 303. It should be appreciated that, although the illustrated embodiment of flow 300 illustrates collection of optical sensor data in parallel with electromagnetic sensor data, such data may be collected sequentially according to some embodiments.

Figure 4A:
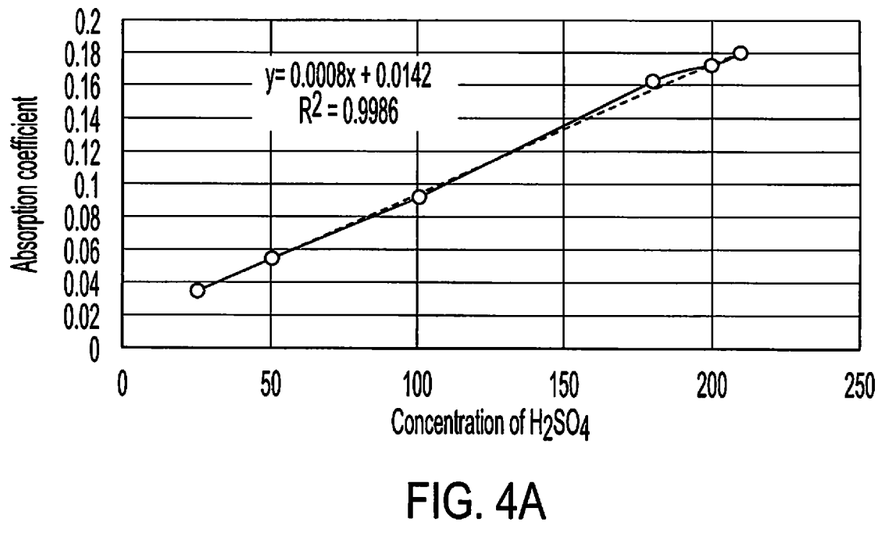
FIG. 4A shows graph of the absorption coefficient of $H_2SO_4$ from an optical sensor implementation used by a cooperative optical and electromagnetic material concentration detector of embodiments of the invention.

At block 302 of the embodiment illustrated in FIG. 3, optical sensor 111 operates to collect data that is optically derived from the sample material. For example, optical sensor 111 may operate under control of processor 121 to measure an optical aspect of a solution by outputting a voltage signal generated by optical receiver 212 in response to light received from light source 211 through a sample of material within sample cavity 213. The voltage signal may, for example, correspond to absorption of light from light source 211 by the $H_2SO_4$ in the sampled electrolytic solution, and thus may correspond to a concentration of $H_2SO_4$ therein. An example graph of the absorption coefficient of $H_2SO_4$ from an embodiment of optical sensor 111 is shown in FIG. 4A.

To provide temperature compensation with respect to the optical sensor measurements, temperature data is collected at block 302 of the illustrated embodiment of flow 300. For example, temperature sensor 113 may operate under control of processor 121 to output digital data generated (e.g., using an ADC internal to temperature sensor 113) in response to the temperature of sampled material in contact with a portion of the temperature sensor for use in resolving issues with respect to temperature effects on the optical measurement.

Figure 4B:
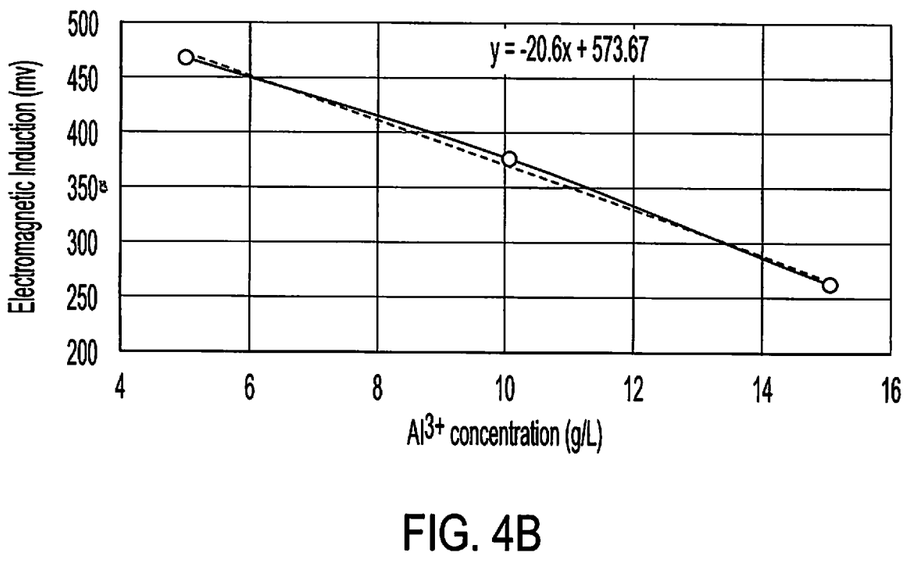
FIG. 4B shows a graph of the relationship between $Al^{3+}$ concentration and electromagnetic induction from an electromagnetic sensor implementation used by a cooperative optical and electromagnetic material concentration detector of embodiments of the invention.

At block 303 of the embodiment illustrated in FIG. 3, control unit 120 operates to collect data from electromagnetic sensor 112. For example, electromagnetic sensor 112 may operate under control of processor 121 to measure an electromagnetic aspect of a solution by outputting digital data generated (e.g., using an ADC internal to electromagnetic sensor 113) in response to an electromotive force detected by induction sensor 221 when in proximity to particular materials within sample cavity 222. The electromotive force may, for example, correspond to the electromagnetic conductivity of the sampled electrolyte solution, as contributed to by both the $SO_4^{2-}$ ions of the sulfuric acid and $Al^{3+}$ ions in the sampled electrolytic solution, and thus may correspond to the concentrations of $H_2SO_4$ and $Al^{3+}$. An example graph of the relationship between $Al^{3+}$ concentration and electromagnetic induction from an embodiment of electromagnetic sensor 112 is shown in FIG. 4B.

To provide temperature compensation with respect to the measurements, temperature data is collected at block 303 of the illustrated embodiment of flow 300. For example, a temperature sensor internal to electromagnetic sensor 112 may operate under control of processor 121 to output digital data generated (e.g., using an ADC internal to the temperature sensor and/or the electromagnetic sensor) in response to the temperature a portion of the temperature sensor in contact with a sensor element of electromagnetic sensor 112 for use in resolving issues with respect to temperature effects on the electromagnetic measurement.

The data collected by the sensors of sensor unit 110, and thus provided to control unit 120, of cooperative op-el mat-con detector 100 of embodiments may comprise various forms of the sampled data, such as instantaneous measurement data, measurement data over some period of time, data regarding measured variations, etc. For example, as shown above, electromagnetic induction data provided by electromagnetic sensor 112 can be affected by $H_2SO_4$ and $Al^{3+}$ at the same time, especially when concentrations are varying. Accordingly, optical sensor 111 of embodiments may be controlled to provide $H_2SO_4$ variation data (e.g., data showing variation of $H_2SO_4$ in the sampled electrolyte solution over time, such as measurement of $H_2SO_4$ over a period of 10 or more minutes). Additionally or alternatively, logic of control unit 120 (e.g., logic executed by processor 121) may derive various forms of data from sampled data provided by one or more of the sensors. For example, in accordance with embodiments of the invention processor 121 may compute $H_2SO_4$ concentration from instantaneous data regarding optical data provided by optical sensor 111.

Data provided by the sensors of sensor unit 110 is transmitted to control unit 120 at block 304 of the illustrated embodiment. For example, data lines and/or other componentry (e.g., control and signal amplification circuitry 124, ADC 125, etc.) of sensor unit 110 and control unit 120 may be used to provide digital data to processor 121 for storage (e.g., within memory 122) and/or processing (e.g., to determine concentrations of one or more materials in accordance with concepts herein). Accordingly, in operation according to embodiments, control unit 120 receives data from optical sensor 111, electromagnetic sensor 112, and temperature sensor 113. In particular, processor 121 may operate under control of an instruction set to receive digital data regarding variation of $H_2SO_4$ in the sample solution provided by optical sensor 111, digital data regarding the temperature of the sample solution from temperature sensor 113, and digital data regarding an electromagnetic signal response such as an electromotive force resulting from the concentrations of $H_2SO_4$ and $Al^{3+}$ in the sample solution and temperature data from electromagnetic sensor 112. Such data may be collected by the sensors and/or received by the processor on demand, repeatedly throughout a sampling period, continuously, etc., as appropriate for the particular situation in which it is being processed and analyzed.

At block 305 of flow 300 illustrated in FIG. 3, cooperative op-el mat-con detector 100 of embodiments uses data collected by the sensors to determine concentrations of $H_2SO_4$ and $Al^{3+}$ in the sample solution. In particular, processor 121 of embodiments operates under control of an instruction set to use data provided by both optical sensor 111 and electromagnetic sensor 112 to determine a concentration of $Al^{3+}$ in the sampled electrolyte solution. In processing the data to determine concentrations of $Al^{3+}$, logic of the aforementioned instruction set executed by processor 121 may subtract variation data of $H_2SO_4$ obtained or derived from the optical sensor from electromagnetic conductivity data obtained or derived from the electromagnetic sensor to determine a concentration of $Al^{3+}$. Concentrations of $H_2SO_4$ may be determined by logic of processor 121 from $H_2SO_4$ obtained or derived from the optical sensor.

Processing the data to determine concentrations of $Al^{3+}$ and $H_2SO_4$ according to embodiments may include performing various pre-processing and/or post-processing steps with respect to the data collected by the sensors and/or received by the processor. For example, logic executed by processor 121 of embodiments may perform temperature compensation, using data provided from one or more temperature sensors (e.g., temperature sensor 113), with respect to the data provided by optical sensor 111 and/or electromagnetic sensor 112, such as to compensate for the effects of temperature on operation of the detector and/or components thereof. Additionally or alternatively, logic executed by processor 121 of embodiments may perform normalization with respect to the data provided by optical sensor 111 and electromagnetic sensor 112, such as to facilitate subsequent combining operations with respect to measurement data provided by each of the optical and electromagnetic sensors. Further detail regarding processing of the data in accordance with exemplary embodiments of cooperative op-el mat-con detector 100 of embodiments is discussed below with reference to the flow diagram of FIG. 5.

Figure 5:
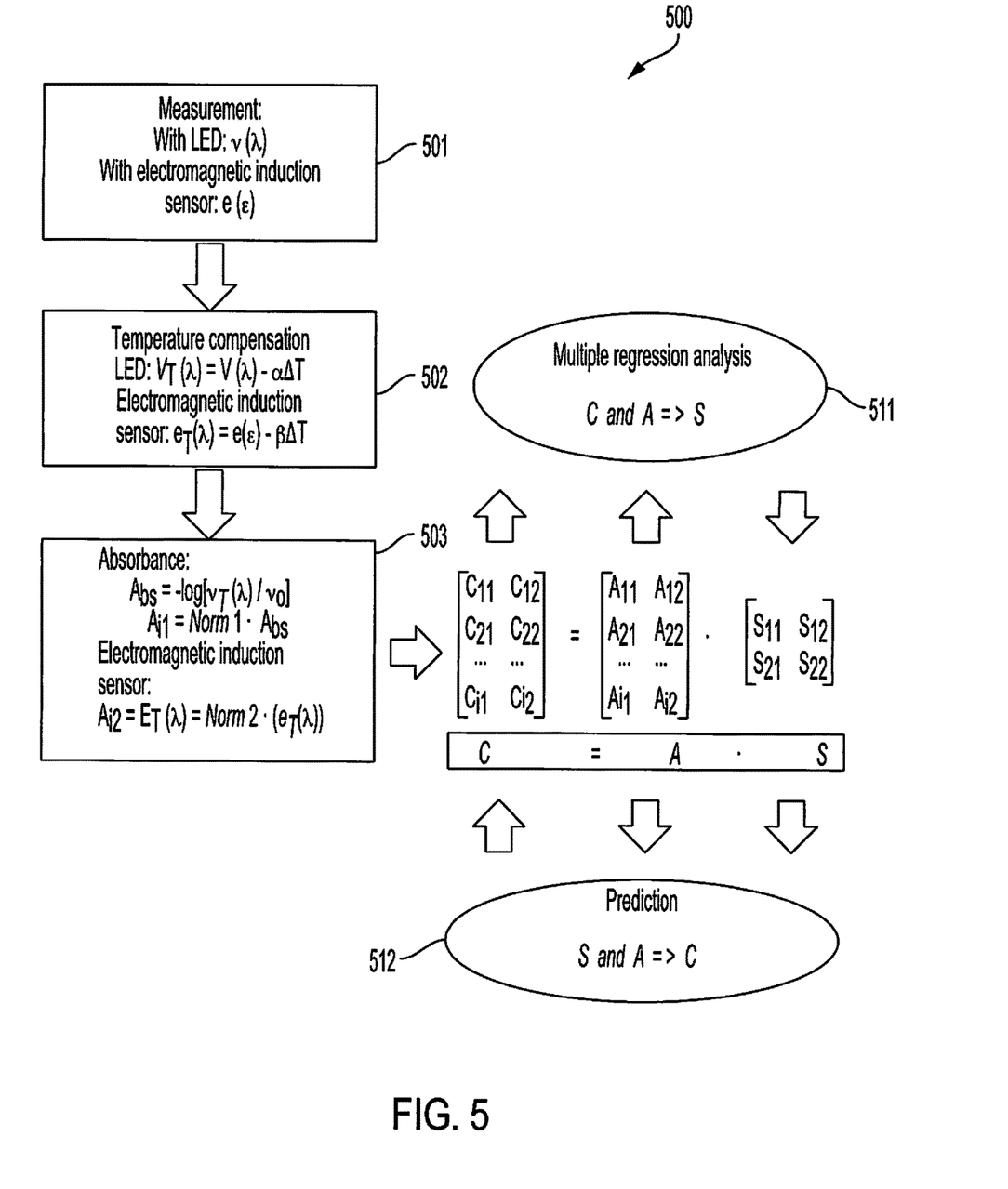
FIG. 5 shows a flow diagram of processing of the data by a cooperative optical electromagnetic material concentration detector of embodiments of the invention.

Referring now to FIG. 5, an exemplary flow for processing sensor data captured by cooperative op-el mat-con detector 100 to determine concentrations of $H_2SO_4$ and $Al^{3+}$ according to embodiments of the invention is shown. Processing flow 500 of the illustrated embodiment may be utilized both with respect to calibration of cooperative op-el mat-con detector 100 for use of the sensors thereof with respect to particular materials to be sampled and with respect to operation of cooperative op-el mat-con detector 100 in determining material concentrations. In the example illustrated in FIG. 5, v is voltage intensity, $v_0$ is voltage intensity from pure water, $v_T$ is voltage intensity after temperature compensation, e is electromotive force, T is temperature, $\alpha$ is temperature coefficient for LED, $\beta$ is temperature coefficient for electromagnetic induction sensor, A is a measured value matrix (containing both absorbance and induction) C is a concentration matrix, and S is a correction matrix.

In calibrating cooperative op-el mat-con detector 100 of embodiments according to flow 500, measurements with respect to solutions having different, known concentrations of material (e.g., solutions having known concentrations of $H_2SO_4$ and $Al^{3+}$, with a first solution having high $H_2SO_4$ and low $Al^{3+}$ concentrations, a second solution having optimum $H_2SO_4$ and $Al^{3+}$ concentrations, a third solution having low $H_2SO_4$ and high $Al^{3+}$, etc.) are made using optical sensor 111 and electromagnetic sensor 112 at block 501. Thereafter, temperature compensation with respect to the optical sensor and electromagnetic sensor data according to block 502 and normalization of the optical sensor and electromagnetic sensor data according to block 503 is provided. The temperature compensated and normalized data is provided as measured value matrix A in flow 500. As the concentrations of the materials in the sampled solutions are known in this exemplary calibration operation of cooperative op-el mat-con detector 100, the data of concentration matrix C is known. Accordingly, regression analysis (e.g., linear regression analysis or liner fitting analysis) performed with respect to the data of measured value matrix A and concentration matrix C is used to determine correction matrix S at block 511. This correction matrix provides calibration parameters for the sensors of cooperative op-el mat-con detector 100 with respect to the materials being sampled, and is later used according to embodiments with respect to measurements of unknown concentrations of material.

In operation of cooperative op-el mat-con detector 100 of embodiments to determine material concentrations according to flow 500, measurements with respect to solutions having unknown concentrations of material (e.g., solutions having unknown concentrations of $H_2SO_4$ and $Al^{3+}$, where the concentrations of either or both materials may be varying over time) are made using optical sensor 111 and electromagnetic sensor 112 at block 501. Thereafter, temperature compensation with respect to the optical sensor and electromagnetic sensor data according to block 502 and normalization of the optical sensor and electromagnetic sensor data according to block 503 is provided. The temperature compensated and normalized data is provided as measured value matrix A in flow 500. Correction matrix S was previously determined in calibration operation according to embodiments of the invention. Accordingly, regression analysis (e.g., linear regression analysis or liner fitting analysis) performed with respect to the data of measured value matrix A and correction matrix S is used at block 512 to determine concentration matrix C, wherein the data of concentration matrix C provides concentration measurement data for the material (e.g., $H_2SO_4$ and $Al^{3+}$).

Figure 6A:
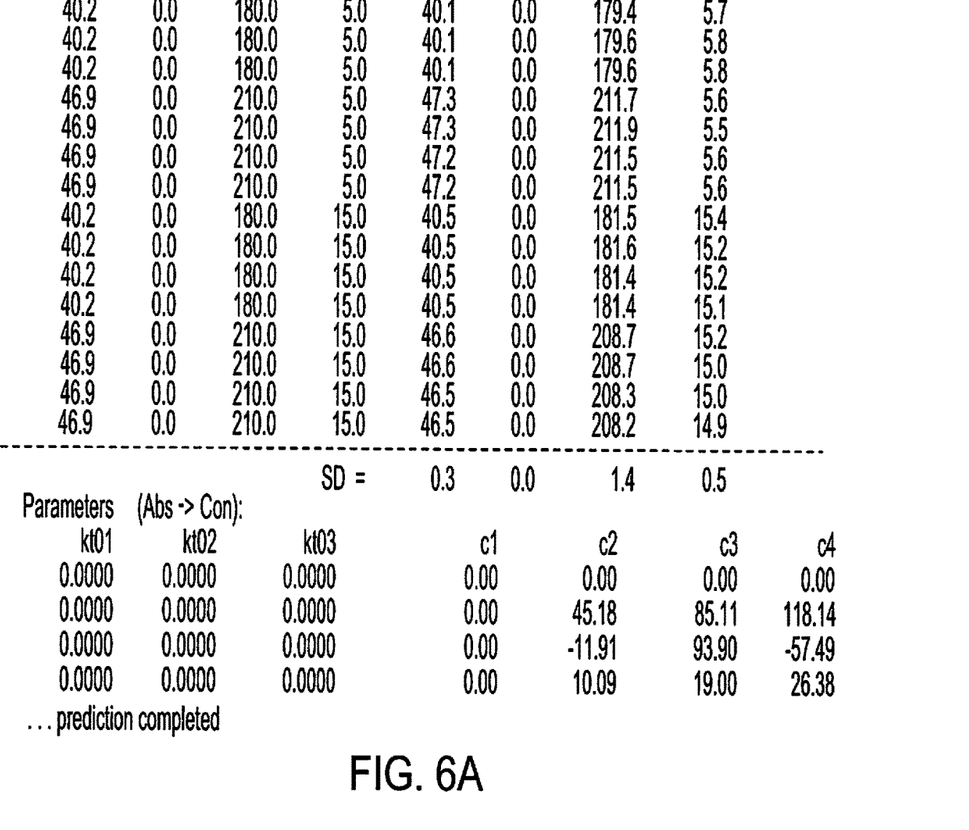
FIGS. 6A and 6B show results for calibration and prediction trials performed a prototype cooperative optical electromagnetic material concentration detector of embodiments of the invention.
Figure 6B:
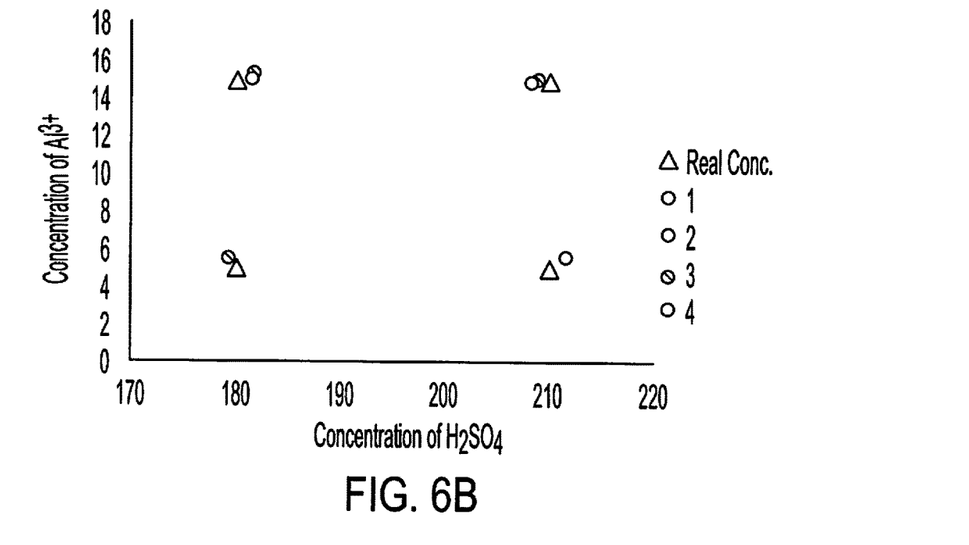

Results for calibration and prediction trials performed in accordance with the flows of FIGS. 4 and 5, using a prototype cooperative op-el mat-con detector embodiment in accordance with FIGS. 1 and 2A, are shown in FIGS. 6A and 6B. As shown in the experimental results, the concentrations of both $H_2SO_4$ (160-230 g/L) and $Al^{3+}$ (3-20 g/L) changes simultaneously. However, in operation according to the exemplary embodiment of the trials, the inter-group error for is $H_2SO_4$ is about 1.5 g/L and the $Al^{3+}$ fluctuations are 0.1 to 0.5 g/L. It can readily be appreciated that the results provided by a cooperative op-el mat-con detector in accordance with concepts of the present invention can be accepted by the industry, such as for use in the exemplary anodizing process.

As can be seen by the foregoing, cooperative op-el mat-con detector 100 of embodiments is operable to determine concentrations of $H_2SO_4$ and $Al^{3+}$ online by a combination of optical absorption and electromagnetic induction when optical sensor 111 is ineffective in directly or solely detecting a concentration of $Al^{3+}$ and electromagnetic sensor 112 is ineffective in accurately detecting a concentration of $Al^{3+}$ when both $H_2SO_4$ and $Al^{3+}$ are present, particularly when concentrations of $H_2SO_4$ are varying.

It should be appreciated, however, that cooperative op-el mat-con detectors in accordance with the concepts herein may be utilized with respect to materials and processes other than those of the examples given above. For example, operation of a cooperative op-el mat-con detector of the above exemplary embodiments is not limited to use with respect to anodizing processes, but may be utilized with respect to anodizing, electroplating, and/or other metal treatment processes. Embodiments of a cooperative op-el mat-con detector may, for example, be used for treated waste water and rewash water.

Treated waste water and rewash water may be utilized in various ways to provide water savings, such to increase manufacturing capacity, reduce costs for industries, etc. For example, rewash water may be used to control the amount of water used in cleaning processes. Similarly, treated waste water may be recycled for use in cleaning processes. As a specific example, although pipe water may have an average concentration of metal ions on the order of 0.01 mg/L, treated waste water may have an average concentration of metal ions on the order of 1 mg/L and rewash water may have an average concentration of metal ions on the order of 100 mg/L. Daily water consumption of an electroplating factory without water quality monitoring system may, for example, be 600 tons in some situations. After using smart water monitoring as may be provided in accordance with the concepts of the present invention, the water consumption can be reduced to 250 tons in an electroplating factory situation previously consuming 600 tons without a water quality monitoring system. Accordingly, monitoring and controlling the quality of treated waste water and rewash water may be desirable to reduce or eliminate harm to human health and the environment, to reduce pollution from the source, improve resource efficiency, reduce or avoid the generation and emission of pollutants in production, and/or the like. Moreover, such water monitoring can be used to increase the manufacturing capacity and reduce costs (e.g., $7.25/ton in some situations) as the industrial water emissions is limited. Treated waste water and rewash water may thus present an excellent use case for metal ion concentration detection in accordance with embodiments of the invention.

Conventional techniques for water quality control with respect to treated waste water or rewash water have typically only used conductivity sensors capable of detecting the total concentrations of ions or salt content. These measurements are affected by other materials in the water, such as acid. Accordingly, monitoring and control of water quality using such conventional techniques has generally provided somewhat inaccurate measurement of the concentrations of individual ions or salt content in the water.

Cooperative op-el mat-con detectors of embodiments of the invention, however, provide excellent candidates for detection of material concentrations in treated waste water and rewash water. For rewash water (100 mg/L), a cooperative op-el mat-con detector may be directly connected with the washing water in the cleaning tanks to record and analyze the water quality, which is convenient for monitoring. For treated waste water (1 mg/L), a cooperative op-el mat-con detector may implement high sensitivity configuration (e.g., using a relatively large flow of sample material or using a relatively large optical path of the sample cavity) to achieved the measurement of low concentration of acid and metal ions. For example, a cooperative op-el mat-con detector implementation consistent with the above examples may implement an optical sensor to measure organic materials, acids, etc. present in the water, while cooperative operation with respect to an optical sensor and an electromagnetic sensor may be implemented to measure the metal ions present in the water. This provides excellent accuracy with respect to measurement of the metal ions, and presents a considerable improvement over the conventional techniques. Accordingly, monitoring and control of water quality using a cooperative op-el mat-con detector of embodiments provides better water efficiency than that provided by conventional techniques.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A system for determining concentrations of one or more materials in a solution, the system comprising:
   an optical sensor configured to measure an optical aspect of the solution associated with a first material of the one or more materials;
   an electromagnetic sensor configured to measure an electromagnetic aspect of the solution associated with the first material and a second material of the one or more materials, wherein the optical sensor and the electromagnetic sensor are disposed in a parallel configuration in a sample flow path used for sampling the solution; and
   a processor having logic configured to determine a concentration of the second material using a combination of material data derived from the optical aspect measured by the optical sensor and material data derived from the electromagnetic aspect measured by the electromagnetic sensor.

2. The system of claim 1, wherein the optical sensor is ineffective in directly detecting the concentration of the second material due at least in part to a physical property of the second material, and wherein the electromagnetic sensor is ineffective in accurately detecting the concentration of the second material when both the first and second materials are present in the solution.

3. The system of claim 2, wherein the second material is metal ions.

4. The system of claim 3, wherein the first material is an acid.

5. The system of claim 4, wherein the metal ions comprise aluminum ions, wherein the acid comprises sulfuric acid, and wherein the solution comprises a solution used in a metal treatment process.

6. The system of claim 3, wherein the solution is water having pollutants comprised of the metal ions.

7. The system of claim 1, wherein the logic of the processor is configured to subtract the material data derived from the optical aspect measured by the optical sensor from the material data derived from the electromagnetic aspect measured by the electromagnetic sensor to determine the concentration of the second material when the solution contains only two unknown chemicals.

8. The system of claim 1, wherein the logic of the processor is configured to implement linear regression analysis or liner fitting analysis to determine the concentration of the second material when the solution contains three or more unknown chemicals.

9. The system of claim 1, further comprising:
   one or more temperature sensors, wherein the logic of the processor is configured to provide temperature compensation for at least one of the material data derived from the optical aspect measured by the optical sensor and the material data derived from the electromagnetic sensor using data derived from the one or more temperature sensors.

10. The system of claim 9, wherein the logic of the processor is configured to provide normalization for the material data derived from the optical aspect measured by the optical sensor and the material data derived from the electromagnetic sensor.

11. The system of claim 1, wherein the sample flow path of the parallel configuration provides different flow rates of the sample, different sample volumes of the sample, or a combination thereof for the optical sensor and the electromagnetic sensor.

12. The system of claim 1, wherein the optical sensor comprises a light emitting diode (LED) optical sensor configuration with a light emitter and an optical receiver of the LED optical sensor configuration are disposed in juxtaposition across a sample cavity at a width in the range of 0.01-50 mm, and wherein the electromagnetic sensor comprises an induction sensor configuration with an induction sensor disposed in proximity to a sample cavity sized for containing an appropriate amount of the sample for induction sensing.

13. A method for determining concentrations of one or more materials in a solution, the method comprising:
   measuring an optical aspect of the solution associated with a first material of the one or more materials using an optical sensor;
   measuring an electromagnetic aspect of the solution associated with the first material and a second material of the one or more materials using an electromagnetic sensor, wherein the optical sensor and the electromagnetic sensor are disposed in a parallel configuration in a sample flow path used for sampling the solution; and
   determining, using logic executed by a processor-based system, a concentration of the second material from a combination of material data derived from the optical aspect measured by the optical sensor and material data derived from the electromagnetic aspect measured by the electromagnetic sensor.

14. The method of claim 13, wherein the determining the concentration of the second material comprises:
   normalizing material data derived from the optical aspect measured by the optical sensor and material data derived from the electromagnetic sensor;
   forming a matrix from data generated by combining the material data derived from the optical aspect measured by the optical sensor and the material data derived from the electromagnetic aspect measured by the electromagnetic sensor; and
   predicting concentrations of the second material using the matrix.

15. The method of claim 14, further comprising:
   deriving a correction matrix by measuring the optical aspect of the solution associated with the first material for known concentrations of the first material using the optical sensor and measuring the electromagnetic aspect of the solution associated with the first and second materials for known concentrations of the first and second materials using the electromagnetic sensor.

16. The method of claim 13, wherein the optical sensor is ineffective in directly detecting the concentration of the second material due at least in part to a physical property of the second material, and wherein the electromagnetic sensor is ineffective in accurately detecting the concentration of the second material when both the first and second materials are present in the solution.

17. The method of claim 16, wherein the second material is metal ions.

18. The method of claim 17, wherein the first material is an acid.

19. The method of claim 18, wherein the metal ions comprise aluminum ions, wherein the acid comprises sulfuric acid, and wherein the solution comprises a solution used in a metal treatment process.

20. The method of claim 17, wherein the solution is water having pollutants comprised of the metal ions.

21. The method of claim 13, wherein the determining the concentration of the second material comprises:
    subtracting, using the logic executed by the processor-based system, the material data derived from the optical aspect measured by the optical sensor from the material data derived from the electromagnetic aspect measured by the electromagnetic sensor to determine the concentration of the second material when the solution contains only two unknown chemicals.

22. The method of claim 13, wherein the determining the concentration of the second material comprises:
    implementing, using the logic executed by the processor-based system, linear regression analysis or liner fitting analysis to determine the concentration of the second material when the solution contains three or more unknown chemicals.

23. The method of claim 13, further comprising:
    providing temperature compensation for at least one of the material data derived from the optical aspect measured by the optical sensor and the material data derived from the electromagnetic sensor using data derived from one or more temperature sensors.

24. The method of claim 23, further comprising:
    providing normalization for material data derived from the optical aspect measured by the optical sensor and material data derived from the electromagnetic sensor.

25. The method of claim 13, wherein the sample flow path of the parallel configuration provides different flow rates of the sample, different sample volumes of the sample, or a combination thereof for the optical sensor and the electromagnetic sensor.

26. The method of claim 13, wherein the optical sensor comprises a light emitting diode (LED) optical sensor configuration with a light emitter and an optical receiver of the LED optical sensor configuration are disposed in juxtaposition across a sample cavity at a width in the range of 0.01 mm to 50 mm, and wherein the electromagnetic sensor comprises an induction sensor configuration with an induction sensor disposed in proximity to a sample cavity sized for containing an appropriate amount of the sample for induction sensing.

27. A system for determining concentrations of one or more materials in a solution, the system comprising:
    an optical sensor unit including an optical sensor and a sample cavity and configured to measure an optical aspect of the solution associated with a first material of the one or more materials, wherein the optical sensor includes a light emitting diode (LED) emitter and an optical receiver disposed in juxtaposition across the sample cavity at a width in the range of 0.01 mm to 50 mm;
    an electromagnetic sensor unit including an induction sensor and a sample cavity and configured to measure an electromagnetic aspect of the solution associated with the first material and a second material of the one or more materials, wherein the induction sensor is disposed in proximity to the sample cavity and the sample cavity is sized for containing an appropriate amount of the sample for induction sensing, and wherein the optical sensor and the electromagnetic sensor are disposed in a parallel configuration in a sample flow path used for sampling the solution that provides different flow rates of the sample, different sample volumes of the sample, or a combination thereof for the optical sensor and the electromagnetic sensor;
    at least one temperature sensor;
    a processor having logic configured to provide temperature compensation for at least one of material data derived from the optical aspect measured by the optical sensor and material data derived from the electromagnetic sensor using data derived from the at least one temperature sensor, to normalize the material data derived from the optical aspect measured by the optical sensor and the material data derived from the electromagnetic sensor, and to determine a concentration of at least one of the first material or the second material at least in part by either subtracting the material data derived from the optical aspect measured by the optical sensor from the material data derived from the electromagnetic aspect measured by the electromagnetic sensor or implementing linear regression analysis or liner fitting analysis.

* * * * *